(12) United States Patent
Scheibel et al.

(10) Patent No.: US 12,409,074 B2
(45) Date of Patent: Sep. 9, 2025

(54) CONFORMABLE DRESSING

(71) Applicant: Solventum Intellectual Properties Company, Maplewood, MN (US)

(72) Inventors: Krystal J. Scheibel, Minneapolis, MN (US); Kristopher E. Hunter, Woodbury, MN (US); Steven B. Heinecke, New Richmond, WI (US)

(73) Assignee: Solventum Intellectual Properties Company, Maplewood, MN (US)

( * ) Notice: Subject to any disclaimer, the term of this patent is extended or adjusted under 35 U.S.C. 154(b) by 473 days.

(21) Appl. No.: 17/599,059

(22) PCT Filed: Mar. 19, 2020

(86) PCT No.: PCT/IB2020/052552
§ 371 (c)(1),
(2) Date: Sep. 28, 2021

(87) PCT Pub. No.: WO2020/201879
PCT Pub. Date: Oct. 8, 2020

(65) Prior Publication Data
US 2022/0175585 A1 Jun. 9, 2022

Related U.S. Application Data (60) Provisional application No. 62/827,400, filed on Apr. 1, 2019.

(51) Int. Cl.
*A61F 13/02* (2024.01)
(52) U.S. Cl.
CPC ...... *A61F 13/0233* (2013.01); *A61F 13/0236* (2013.01)

(58) Field of Classification Search
CPC ........ A61F 13/00; A61F 13/02; A61F 13/023; A61F 13/0246; A61F 13/0226;
(Continued)

(56) References Cited

U.S. PATENT DOCUMENTS

| RE24,906 E | 12/1960 | Ulrich |
|---|---|---|
| 3,389,827 A | 6/1968 | Abere |

(Continued)

FOREIGN PATENT DOCUMENTS

| CN | 101896145 A | 11/2010 |
|---|---|---|
| CN | 105025969 A | 11/2015 |

(Continued)

OTHER PUBLICATIONS

Machine translation of EP 2752176 A1 (Year: 2014).*
(Continued)

*Primary Examiner* — Caitlin A Carreiro (57) ABSTRACT

When thin-film dressings are used to secure a device, the dressing might need to stretch in some areas to accommodate varying sizes of a device, while remaining stiffer in some areas to limit stretching of the materials. Excessive stretching of the materials can cause the dressing to peel away from the skin or cause the underlying device to not be sufficiently secured. The disclosed dressing can be used to secure a device and includes perforations near the device securement area to allow for isolated regions of adjustability to accommodate a secure fit between the dressing and device.

18 Claims, 4 Drawing Sheets

(58) Field of Classification Search
CPC .............. A61F 13/0233; A61F 13/0236; A61F 13/0269; A61F 2013/00582; A61M 25/02; A61M 25/0612; A61M 2005/1586
USPC .................. 602/42, 54, 58, 60; 604/164.04; 128/847, 877, DIG. 26
See application file for complete search history.

(56) References Cited

U.S. PATENT DOCUMENTS

| | | | |
|---|---|---|---|
| 3,645,835 | A | 2/1972 | Hodgson |
| 4,112,213 | A | 9/1978 | Waldman |
| 4,310,509 | A | 1/1982 | Berglund |
| 4,323,557 | A | 4/1982 | Rosso |
| 4,595,001 | A | 6/1986 | Potter |
| 4,737,410 | A | 4/1988 | Kantner |
| 4,941,882 | A | 7/1990 | Ward |
| 5,088,483 | A | 2/1992 | Heinecke |
| 5,160,315 | A | 11/1992 | Heinecke |
| 5,230,701 | A | 7/1993 | Meyer |
| 5,968,000 | A | 10/1999 | Harrison |
| 6,124,521 | A | 9/2000 | Roberts |
| 6,685,682 | B1 | 2/2004 | Heinecke |
| 6,994,904 | B2 | 2/2006 | Joseph |
| 7,025,749 | B2 | 4/2006 | Propp |
| 7,294,752 | B1 | 11/2007 | Propp |
| 8,212,101 | B2 | 7/2012 | Propp |
| 2010/0121282 | A1* | 5/2010 | Propp .................... A61M 25/02 602/54 |
| 2010/0198161 | A1* | 8/2010 | Propp .................. A61F 13/0269 604/180 |
| 2012/0121282 | A1 | 5/2012 | Oba |
| 2014/0005607 | A1* | 1/2014 | Elsamahy ............. A61F 13/023 604/180 |
| 2015/0014949 | A1 | 1/2015 | Dittman |
| 2016/0015570 | A1* | 1/2016 | Heinecke ............ A61F 13/0236 602/58 |
| 2016/0263351 | A1* | 9/2016 | Schutz .................. A61M 25/02 |

FOREIGN PATENT DOCUMENTS

| | | | |
|---|---|---|---|
| EP | 1121679 | 8/2001 | |
| EP | 2752176 A1 * | 7/2014 | ....... A61F 13/00991 |
| SE | 532495 C2 * | 2/2010 | ......... A61F 13/0203 |
| WO | WO 2010-056541 | 5/2010 | |
| WO | WO 2010-056543 | 5/2010 | |
| WO | WO 2013-150487 | 10/2013 | |
| WO | WO 2015-035238 | 3/2015 | |
| WO | WO 2019-073326 | 4/2019 | |

OTHER PUBLICATIONS

Machine translation of SE 532495 C2 (Year: 2010).*
International Search Report for PCT International Application No. PCT/IB2020/052552, mailed on May 29, 2020, 5 pages.

* cited by examiner

CONFORMABLE DRESSING

CROSS REFERENCE TO RELATED APPLICATIONS

This application is a national stage filing under 35 U.S.C. 371 of PCT/IB2020/052552, filed Mar. 19, 2020, which claims the benefit of Provisional Application No. 62/827,400, filed Apr. 1, 2019, the disclosure of which is incorporated by reference in its/their entirety herein.

TECHNICAL FIELD

The present disclosure relates to a conformable dressing comprising a backing layer with a perforation set for enabling controlled elasticity.

BACKGROUND

Transparent film dressings are widely used on skin because they protect the skin by acting as a barrier to contaminating liquids and bacteria. For example, transparent film dressings are available under a number of trade names such as TEGADERM™ (3M Company, St. Paul, MN).

The polymeric films used in those dressings and drapes are conformable, i.e., the films are extremely thin, flexible and supple. They are typically supplied with a releasable protective liner covering the adhesive coated surface of the film. To prevent the adhesive coated film from wrinkling during application, various delivery systems have been proposed to address this problem, such as those disclosed in U.S. Pat. No. 6,685,682.

Thin polymeric films that are flexible and resilient are beneficial when used on skin that flexes, stretches, and retracts. However, for some applications, the high flexibility and resiliency of the thin polymeric film can move and stretch too much causing the film to peel or release from the skin. Therefore, medical dressings have been developed that include stiffer, less conformable material secured to the thin polymeric film. For example, U.S. Pat. No. 5,088,483 discloses an adhesive composite that includes a conformable backing and a permanent adhesive reinforcement around the periphery of the adhesive composite. One example of a commercially available medical dressing with a reinforcement layer is TEGADERM™ IV Advanced Dressing (3M Company, St. Paul MN).

SUMMARY

When thin-film dressings are used to secure a device, the dressing might need to stretch in some areas to accommodate varying sizes of a device, while remaining stiffer in some areas to limit stretching of the materials. Excessive stretching of the materials can cause the dressing to peel away from the skin or cause the underlying device to not be sufficiently secured. The disclosed dressing can be used to secure a device and includes perforations near the device securement area to allow for isolated regions of adjustability to accommodate a secure fit between the dressing and device.

In one embodiment, the dressing comprises a first major surface; second major surface, opposite the first major surface, defined by a perimeter around a body layer, wherein the second major surface comprises an adhesive; and a slot for receiving a device. The slot is an extension of the perimeter within the body layer to a terminal end. The slot is separated by a first and second portion of the body layer.

In one embodiment, the dressing further comprises a first perforation set that extends at least partially through the thickness of the flexible backing layer and extending from the perimeter of the dressing at the slot to within the body layer.

In one embodiment, the body layer further comprises a support material secured to the body layer. In one embodiment, the support material covers a portion of the body layer. In one embodiment, the support material extends to the perimeter. In one embodiment, the support material is less elastic than the body layer.

In one embodiment, the first perforation set extends through the thickness of the support material. In one embodiment, the slot extends along a dressing slot axis. In one embodiment, the first and second body portions are symmetrical about the dressing slot axis. In one embodiment, the first perforation set is at the terminal end of the slot. In one embodiment, the first perforation set is at the terminal end of the slot and parallel to the dressing slot axis.

In one embodiment, the dressing further comprises a second perforation set through the body layer. In one embodiment, the second perforation set extends from the perimeter to within the body layer. In one embodiment, the first perforation set has a first end and a second end, and the second perforation set has a first end and a second end. In one embodiment, the first end of the first perforation set is the same as the first end of the second perforation set. In one embodiment, the first end of the first perforation set is different from the first end of the second perforation set. In one embodiment, the first perforation set is substantially perpendicular to the dressing slot axis. In one embodiment, the second perforation set is substantially perpendicular to the dressing slot axis. In one embodiment, the first perforation set extends from the first end at the perimeter through the body layer to the perimeter. In one embodiment, the first perforation set extends from the first end at the perimeter through the body layer to a different portion of the perimeter. In one embodiment, the first perforation set is at the terminal end of the slot, parallel with the dressing slot axis, and extends through the body layer to a different portion of the perimeter.

In one embodiment, a method of securing a device comprises applying the dressing to a device, wherein the device aligns with the slot. In one embodiment, the method further comprises separating at least a portion of the first perforation set adjacent to the device. In one embodiment, the method further comprises applying a tape strip across the slot, underlying the device.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

The disclosed dressing comprises a body layer with a slot for receiving a device. From the perimeter at the slot is at least one perforation set that allows for flexible expansion of the slot to accommodate various sizes of devices, such as tubing.

Figure 1:
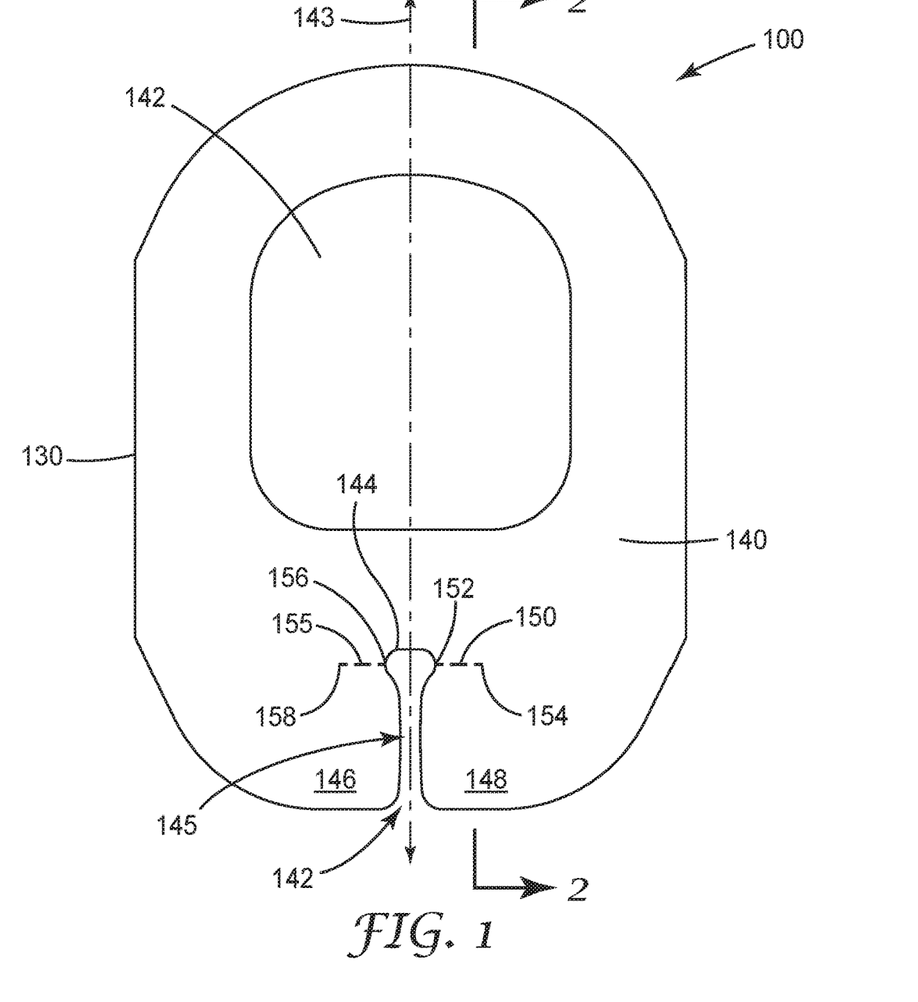
FIG. 1 is a first embodiment of a dressing comprising a first perforation set and second perforation set.
Figure 2:
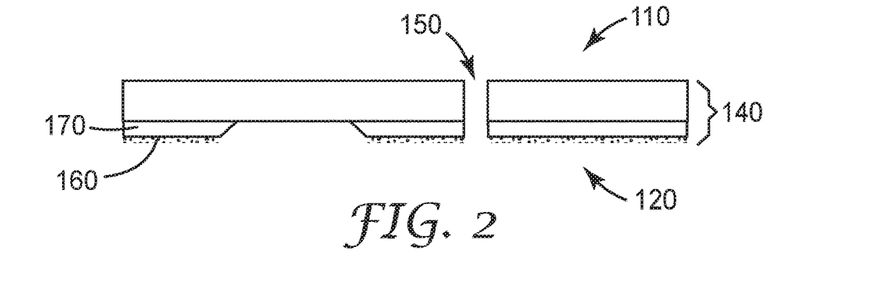
FIG. 2 is a side sectional view of FIG. 1 through line 2-2.
Figure 3:
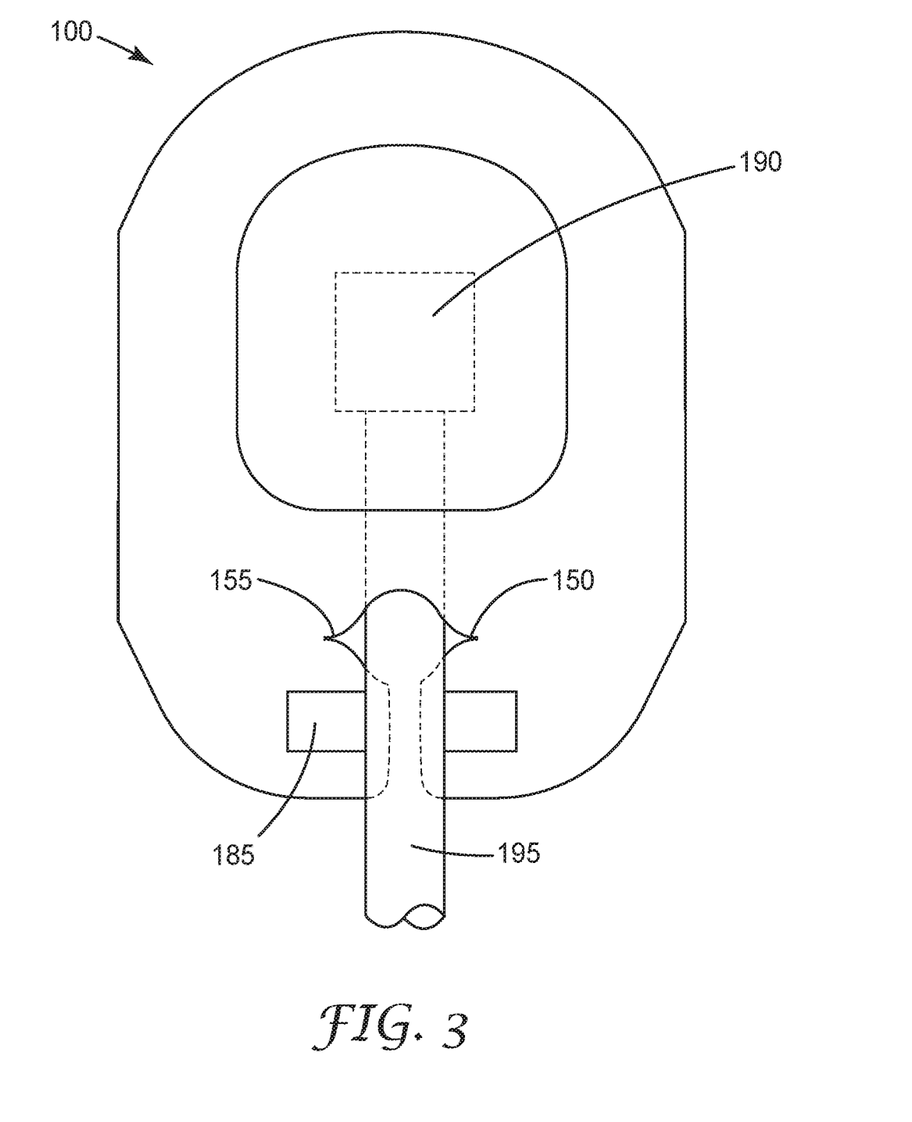
FIG. 3 is the dressing of FIG. 1 with an underlying device at the slot and tape strip across the slot underlying the device.

FIG. 1 is a first embodiment of a dressing 100 comprising a first perforation set 150 and a second perforation set 155, FIG. 2 is a side sectional view of the dressing 100 shown in FIG. 1, and FIG. 3 is the dressing 100 shown with an underlying device 190 and an extending tube 195.

The dressing 100 has a first major surface 110 and second major surface 120, which is opposite the first major surface 110. At least a portion of the second major surface 120 comprises an adhesive 160 (see FIG. 2) for securing the dressing 100 to an underlying substrate, such as skin.

A perimeter 130 surrounds the dressing 100 and defines a body layer 140 of the dressing 100. The body layer 140 is typically a thin, flexible material that can be applied over an irregular, contoured substrate 165, such as skin. The body layer 140 can be a single or multilayer construction and can further comprise an additional support material 170 secured to at least a portion of the body layer 140. Various types of suitable materials for the body layer 140 and support material 170, if included, are described below.

The dressing 100 has a slot 145, which is an extension of the perimeter 130 within a portion of the body layer 140. The slot 145 is separated by a first portion 146 of the body layer 140 and a second portion 148 of the body layer 140. The slot 145 has a width forming a gap between the first portion 146 and the second portion 148 of the body layer 140. The slot 145 has a receiving end 142 that is open and is a separation between the first portion 146 and second portion 148 of the body layer 140, and the slot 145 has a terminal end 144 that is the innermost extension of the slot 145 into the body layer 140. In one embodiment, the slot 145 is linear along a slot axis 143. However, the slot 145 can be of various sizes, shapes, width or lengths so long as it provides a separation between the first portion 145 and second portion 148 of the body layer 140. In this embodiment, the first portion 146 and second portion 148 of the body layer 140 are symmetric about the slot axis 143. In use, the device 190, and tubing 195, will extend through the slot 145.

A first perforation set 150 is at the perimeter 130 at the slot 145. The first perforation set 150 is a set of through cuts with each cut separated from another cut by the body layer 140. The cuts of the first perforation set 150 extend at least partially through the thickness of the body layer 140 to create an area of structural weakness of the body layer 140. In some embodiments, the through cuts of the first perforation set 150 extend entirely through the body layer 140. In some embodiment, the through cuts extend partially into the body layer 140. If the body layer 140 is a multilayer construction, the through cuts could extend entirely through one layer, and not through other layers of the body layer 140. In one embodiment, such as shown in FIG. 1, the cut of the first perforation set 150 is a slit with essentially no width, meaning no material was removed from the body layer 140 during cutting. In one embodiment, the cut of the first perforation set 150 has a width of material removed.

It is understood the individual cuts of a perforation set may be the same length as one another or may be of varying lengths. For example, the length of each cut may graduate from shorter to longer or from longer to shorter. The same with the spacing between each individual cut. may be the same length as one another or may be of varying lengths. For example, the spacing between each individual cut may graduate from shorter to longer or from longer to shorter.

Laterally, the first perforation set 150 extends from a first end 152 at the perimeter 130 at the slot 145 to a second end 154. In this embodiment, the second end 154 is within the body layer 140. The first perforation set 150 can be in a line, an array, or cluster. If the first perforation set 150 is in a line, it can be a straight, angled, or curved line.

The first perforation set 150 can be positioned at or near the terminal end 144 of the slot 145 as shown in FIGS. 1 and 3. The first perforation set 150 can extend at least partially from the perimeter 130 into the body 140 at any angle relative to the dressing slot axis 143. In the embodiment depicted in FIG. 1, the first perforation set 150 extends substantially perpendicular to dressing slot axis 143 into body 140.

The dressing 100 can have more than one perforation set. Any additional perforation sets can have features such as described for the first perforation set. As shown in the embodiment in FIG. 1-3, there is a first perforation set 150 and a second perforation set 155 at the slot 145. The second perforation set 155 is a set of through cuts with each cut separated from another cut by the body layer 140. Similar to the first perforation set, the second perforation set 155 extends at least partially through the thickness of the body layer 140.

Laterally, the second perforation set 155 extends from a first end 156 at the perimeter 130 at the slot 145 to a second end 158. In this embodiment, the second end 158 is within the body layer 140. The second perforation set 155 can be in a line, and array, or cluster. If the second perforation set 155 is in a line, it can be a straight, angled, or curved line. In the embodiment depicted in FIG. 1, the second perforation set 155 extend substantially perpendicular to dressing slot axis 143 into body 140, opposite from the first perforation set 150. In this embodiment, the second perforation set 155 is substantially the same size and shape as the first perforation set 150. It is understood that first and second perforation sets can be different sizes, lengths, shapes from one another. The second perforation set 155 provides an area of weakness in the structural strength of the body layer 140 of the dressing 100 and will cause a break at the second perforation set 155 to expand the side of the slot 145 for a larger tube 195.

In one embodiment, the first perforation set 150, and second perforation set 155, if included, have cut lengths between 0.025 inches and 1.0 inches wide. In one embodiment, the body layer 140 between cuts is between 0.01 inches and 0.05 inches wide.

In use, the dressing 100 is applied over a device 190, like shown in FIG. 3, with a portion of the device 190, such as tubing 195 extending through the slot 145. The tubing 195 size can vary. Therefore, the first perforation set 150 provides an area of weakness in the structural strength of the body layer 140 of the dressing 100 and will cause a break at the first perforation set 150 to expand the side of the slot 145 fora larger tube 195.

Including both a first perforation set 150 and a second perforation set 155, increases the ability to expand the width of the slot 145 to accommodate the device 190 or tubing 195. In one embodiment, the dressing 100 is for placement over an intravenous catheter device 190 with tubing 195. The intravenous device 190 is placed under the body layer 140 of the dressing 100, and the tubing 195 extends through the slot 145. For a large size tubing 195, at least a portion of the first perforation set 150 and/or second perforation set 155 will expand the width of slit 145 to size of the tubing 195.

Optionally, the body layer 140 of the dressing 100 can include a support material 170. The support material 170 secures with at least a portion of the body layer 140. In some embodiments the body layer 140 is very flexible and elastic. The support material 170 can be provided in regions to limit the flexibility and elasticity of the body layer. The support material 170 can be provided to have a flexibility or elasticity in one direction that is different than the flexibility or elasticity in a second direction. This can further help control the overall extensibility and flexibility of the overall dressing.

When included, the support material 170 is secured to the body layer 140, through adhesive, thermal bonding, lamination, or other commonly used securement techniques. The support material 170 provides structural strength to the dressing 100, and therefore, independently, is less elastic than the body layer 140. In one embodiment, the support material 170, independently, has essentially no elasticity, such that is may be unable to stretch and/or it may be unable to recover from a stretch. In one embodiment, the support material 170, may be more elastic in one direction (machine direction) than in the cross direction (transverse direction), but overall it has less elasticity than the body layer 140.

Elasticity can be measured by any number of commonly used means for evaluating stretch and recovery of a material. In one embodiment, the body layer 140 (independent of the support material) has an elongation at break of at least 200%. In one embodiment, the body layer 140 (independent of the support material) has an elongation at break of at least 1000%. In one embodiment, the body layer 140 (independent of the support material) has an elongation at break of less than 500%. In one embodiment, the support material 170 (independent of the backing layer) has an elongation at break of at least 20%. In one embodiment, the support material 170 (independent of the backing layer) has an elongation at break of at least 100%. In one embodiment, the support material 170 has an elongation at break less than 200%.

In the embodiment shown in FIGS. 1-3, a support material 170 extends adjacent the entire perimeter 130 of the dressing 100, but is not continuous across the entire body 140. The support material 170 is not located in the central window 142 of the dressing 100 to allow for a transparent window to view the underlying substrate 165 or device 190. In this embodiment, the support material 170 comprises polymeric film(s), nonwoven fibrous webs, woven fibrous webs, knits, films and other backing materials, which maybe translucent or transparent. The arrangement of the body layer 140 and support material 170 is similar to a 3M Tegaderm IV Advanced Securement Dressing, which includes a nonwoven layer adjacent to a thin polyurethane film. When the support material 170 is included, the perforation sets might be included in only those portion including the support material. Typically, the stiffness or rigidity of the support material will limit the propagation of the perforation opening.

The body layer 140 can be thin, flexible, elastic and a sufficiently impermeable barrier to the passage of liquids and at least some gases, which protects the covered site from external contaminants. Being elastic allows for the body layer 140 to expand, contract, stretch and recover as the underlying substrate, such as skin, moves. The support material 170 can be included in specific areas, like the perimeter 130, to limit flexibility and stretching of the body layer 140. Excessive stretching of the body layer 140 can cause peeling or a loose fit to the underlying device. When a support material 170 is included in the dressing 100, expansion at the slot 145 can be significantly restricted. Therefore, the perforation sets 150, 155 provide for isolated stretching and expansion in the areas with limited ability to stretch due to the support material 170. If a support material 170 is included, the perforation set 150 remains within the areas of the support material 170 to prevent further propagation of the tear.

Figure 4:
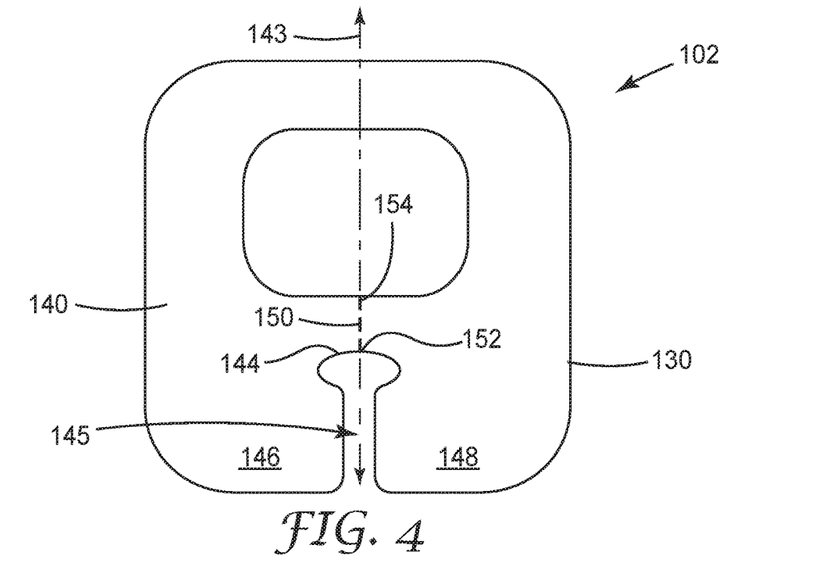
FIG. 4 is another embodiment of a dressing comprising a first perforation set.

FIG. 4 is a second embodiment of a dressing 102. Dressing 102 is substantially similar to the embodiment of the dressing 100 depicted in FIG. 1, and so the same reference numbers are used to identify the same structural elements. However, dressing 102 has only the first perforation set 150 and does not include a second perforation set. Also, the first perforation set 150 extends parallel to dressing slot axis 143 from the apex of the terminal end 144 of slot 145. The first perforation set 150 extends from a first end 152 at the perimeter 130 to a second end 154 within the body layer 140. This arrangement of perforation set 150 allows for selectively tearing along the perforation set 150 to accommodate a catheter of varying sizes and shapes. If a support material 170 is included, the perforation set 150 remains within the areas of the support material 170 to prevent further propagation of the tear.

Figure 5:
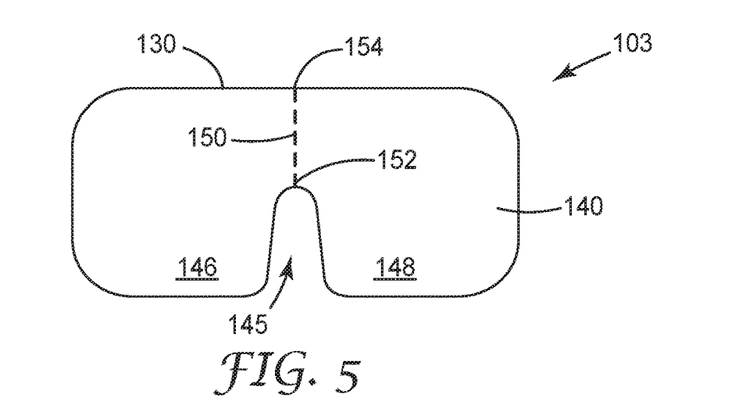
FIG. 5 is another embodiment of a dressing, specifically a tape, comprising a single perforation set.

FIG. 5 is a third embodiment of a dressing 103. In this embodiment, the dressing 103 is a tape strip. The same reference numbers are used to identify the same structural elements as described in FIGS. 1-3. This dressing 103 comprises a first perforation set 150. In this embodiment, the first perforation set 150 extends from a first end 152 adjacent the perimeter 130 at the apex of the terminal end 144 of slot 145 at least partially through the body layer 140 to a second end 154 also on the perimeter 130 along a line substantially parallel to dressing slot axis 143. Slot 145 is positioned in the body 140 such that the portions of the body on either side of slot 145 are symmetric about dressing slot axis 143. Support material is not included. It is understood that the support material could be included over a portion or over the entire dressing. This arrangement of first perforation set 150 allows for selectively tearing along the dressing slot axis for improved coverage of the site around a catheter and for tearing the tape completely to aid in removal of the tape. This dressing 103 can be used in combination with a dressing such as shown in FIG. 1 or FIG. 3 to further secure the device 190, like shown in FIG. 3.

Figure 6:
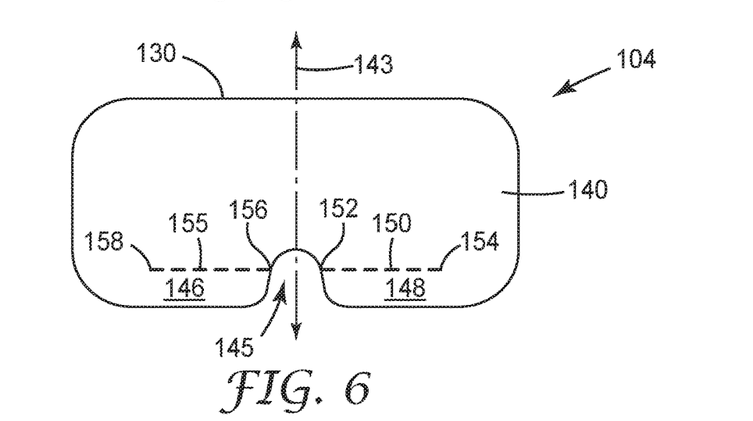
FIG. 6 is another embodiment of a dressing, specifically a tape, comprising a first perforation set and a second perforation set.

FIG. 6 is a fourth embodiment of a dressing 104. In this embodiment, the dressing 104 is a tape strip. The same reference numbers are used to identify the same structural elements as described in FIGS. 1-3. This dressing 104 comprising a first perforation sets 150 and second perforation set 155. In this embodiment, the first perforation sets 150 extend from a first end 152 adjacent the perimeter 130 proximate to the apex of the terminal end 144 of slot 145 to a second end 154 into the body layer 140 along a line substantially perpendicular to dressing slot axis 143. The second perforation sets 155 extend from a first end 156 adjacent the perimeter 130 proximate to the apex of the terminal end 144 of slot 145 to a second end 158 into the body layer 140 along a line substantially perpendicular to dressing slot axis 143. In this embodiment, the first perforation sets 150 and second perforation set 155 are additionally symmetrical about slot 145 and the dressing slot axis 143. Support material is not included. It is understood that the support material could be included over a portion or over the entire dressing. This arrangement of first perforation sets 150 and second perforation set 155 allows for selectively tearing along the dressing slot axis for improved coverage of the site around a catheter and accommodation of catheters of varying sizes and shapes. This dressing 104 can be used in combination with a dressing such as shown in FIG. 1 or FIG. 3 to further secure the device 190, like shown in FIG. 3.

Figure 7:
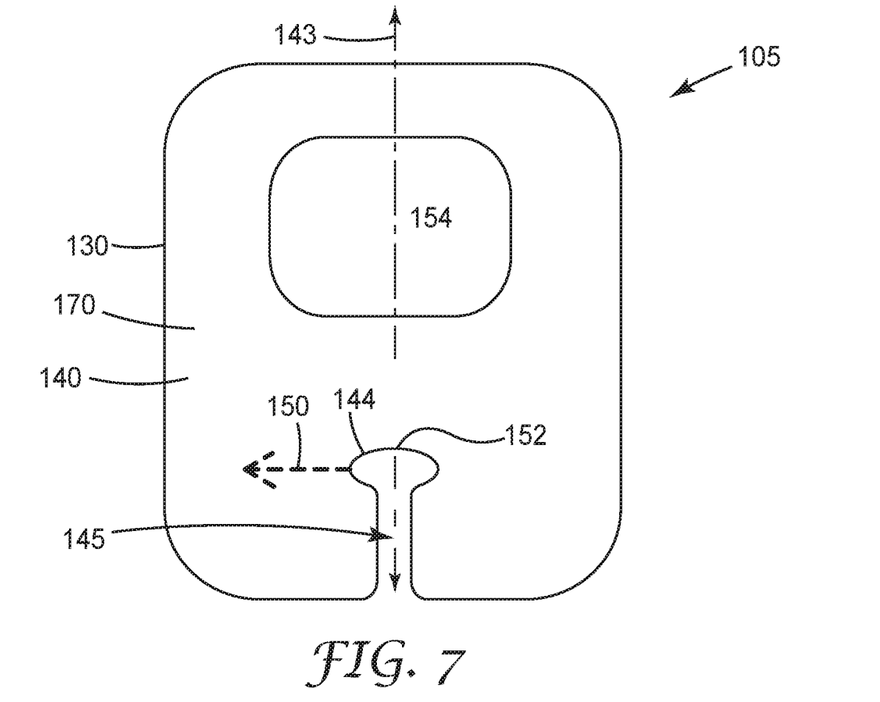
FIG. 7 is another embodiment of a dressing comprising a first perforation set.

FIG. 7 is an embodiment of a dressing 105. Dressing 105 is substantially similar to the embodiment of the dressing 100 depicted in FIG. 1 and dressing 102 depicted in FIG. 4, and so the same reference numbers are used to identify the same structural elements. However, dressing 105 has a first perforation set 150 that extends perpendicular to dressing slot axis 143 from a side of the slot 145. The first perforation set 150 extends from a first end 152 at the perimeter 130 to a second end 154 within the body layer 140. This first perforation set 150 has a portion that extends in a first direction and a second portion that extends in a second direction. This arrangement of first perforation set 150 form an arrow "←" shape. This arrangement of perforation set 150 allows for selectively tearing along the perforation set 150 to accommodate a catheter of varying sizes and shapes.

The dressing disclosed may be made by conventional techniques (e.g., extrusion, solvent casting, calendaring, laminating, adhesive coating, and the like) which are familiar to those skilled in the art. U.S. Pat. No. 6,685,682, the disclosure of which is herein incorporated by reference, discloses constructions and methods for making dressings with backing layers and support material. It will be understood that the perforation sets can be applied using know cutting or perforation techniques to the body layer prior to final construction of the dressing or after final construction of the dressing.

Body Layer

The dressings are useful to provide an impermeable barrier to the passage of liquids and at least some gases. The dressings are well suited for medical application and for securing to skin. Representative barriers for use as the body layer may include non-woven and woven fibrous webs, knits, films, foams, polymeric films. In some embodiments, a transparent substrate is desirable to allow for viewing of the underlying skin or device.

In one embodiment, the body layer has high moisture vapor permeability, but generally impermeable to liquid water so that microbes and other contaminants are sealed out from the area under the substrate. One example of a suitable material is a high moisture vapor permeable film such as described in U.S. Pat. Nos. 3,645,835 and 4,595,001, the disclosures of which are herein incorporated by reference. In high moisture vapor permeable film/adhesive composites, the composite should transmit moisture vapor at a rate equal to or greater than human skin such as, for example, at a rate of at least 300 g/m$^2$/24 hrs at 37° C./100-10% RH, or at least 700 g/m$^2$/24 hrs at 37° C./100-10% RH, or at least 2000 g/m$^2$/24 hrs at 37° C./100-10% RH using the inverted cup method as described in U.S. Pat. No. 4,595,001. Pattern coated adhesives may be used to increase the moisture vapor transmission. In one embodiment, the body layer is an elastomeric polyurethane, polyester, or polyether block amide films. These films combine the desirable properties of resiliency, elasticity, high moisture vapor permeability, and transparency. A description of this characteristic of body layers can be found in issued U.S. Pat. Nos. 5,088,483 and 5,160,315, the disclosures of which are hereby incorporated by reference Commercially available examples of potentially suitable body layers may include the thin polymeric film backings sold under the trade names TEGADERM (3M Company), OPSITE (Smith & Nephew), etc.

In some embodiment, it may be desirable that the body layer is relatively thin to improve conformability. For example, the backing layer may be formed of polymeric films with a thickness of 200 micrometers or less, or 100 micrometers or less, potentially 50 micrometers or less, or even 25 micrometers or less.

Support Material

The support material provides strength to the thin, flexible body layer. The support material therefore has more stiffness and less elasticity than the body layer. The support material may be a coating, such as an adhesive, or may be a self-supporting substrate such as another film, woven, knitted, or nonwoven fabric. For example, U.S. Pat. No. 5,088,483 discloses a permanent adhesive as a reinforcement that could be used as the support material.

In one embodiment, a woven, knitted, or nonwoven fabric used as the support material. One example of nonwoven for the support material is a high strength nonwoven fabric available from E. I. Dupont de Nemours & Company of Wilmington, Delaware under the trademark Sontara. Other suitable nonwoven webs include a hydroentangled polyester fabric available from Veratec, a division of International Paper of Walpole, Mass. Another suitable nonwoven web is the nonwoven elastomeric web described in U.S. Pat. No. 5,230,701, herein incorporated by reference.

Adhesive

Any number of adhesives can be used with the dressing. Suitable adhesives are pressure sensitive and in certain embodiments have a relatively high moisture vapor transmission rate to allow for moisture evaporation. Suitable pressure sensitive adhesives include those based on acrylates, urethane, hydrogels, hydrocolloids, block copolymers, silicones, rubber-based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may be used in the dressings may include adhesives that are typically applied to the skin such as the acrylate copolymers described in U.S. Pat. No. RE 24,906, particularly a 97:3 isooctyl acrylate: acrylamide copolymer. Another example may include a 70:15:15 isooctyl acrylate:ethyleneoxide acrylate:acrylic acid terpolymer, as described in U.S. Pat. No. 4,737,410. Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310, 509 and 4,323,557.

Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

The pressure sensitive adhesives may, in some embodiments, transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904.

Different portions of the dressing may include different adhesives, such as disclosed in U.S. Patent Application Publication 2015/014949 titled "Medical Dressing with Multiple Adhesives." For example, a portion may include an acrylate adhesive while another portion may include a silicone adhesive. In one embodiment, to prevent edge separation, adjacent the perimeter is acrylate adhesive, while near the central portion there is silicone adhesive. In one embodiment, to strongly secure with a device or tubing near the central portion there is acrylate adhesive, while near the perimeter in contact with skin is silicone adhesive.

Optional Components

In some applications, an absorbent material may also be used in conjunction with the dressings described herein. An absorbent material can be any of a variety of materials including, but not limited to, foam, sponge, super absorbent fibers/particles, hydrocolloid compositions, knitted, woven or nonwoven fabrics. The absorbent material can absorb body fluid underlying the dressing.

An optional release liner may be included that covers all or a portion of the adhesives to prevent contamination of the adhesives prior to use. In one embodiment, the package that contains the dressing may serve as a release liner. Suitable release liners can be made of Kraft papers, polyethylene, polypropylene, polyester or composites of any of these materials. In one embodiment, the liners are coated with release agents such as silicones.

An optional carrier may be included that covers all or a portion of the first major surface of the body layer, providing structural support if the dressing is thin and highly flexible. The carrier may be removable from the first major surface once the dressing is placed on skin. The carrier can be constructed of a variety of materials such as fabric that are woven or kitted, nonwoven material, papers, or film. In one embodiment, the carrier is along the perimeter of the first major surface of the dressing and is removable from the first major surface, similar to the carrier used in the 3M Tegaderm™ Transparent Film Dressing, available from 3M Company, St. Paul, MN.

An optional antimicrobial component may be included that is either separate from the adhesive dressing or may be integral with the dressing. The antimicrobial component is placed near or adjacent to the insertion site of the device 190 to inhibit microbial growth in and around the insertion site. The antimicrobial component can be absorbent foam or gel, such as used in a 3M Tegaderm™ CHG I.V. Securement Dressing, available from 3M Company.

Although specific embodiments have been shown and described herein, it is understood that these embodiments are merely illustrative of the many possible specific arrangements that can be devised in application of the principles of the invention. Numerous and varied other arrangements can be devised in accordance with these principles by those of skill in the art without departing from the spirit and scope of the invention. The scope of the present invention should not be limited to the structures described in this application, but only by the structures described by the language of the claims and the equivalents of those structures.

What is claimed is:

1. A dressing comprising:
   a body layer including a first major surface comprising an adhesive, and a second major surface opposite the first major surface, the body layer defining a first perimeter portion;
   a slot defined in the body layer by a second perimeter portion of the body layer and extending from the first perimeter portion, wherein the slot extends along a slot axis from the first perimeter portion, and wherein the slot is defined by a receiving end and a terminal end in the body layer; and
   a first perforation set extending from the second perimeter portion at a location between the receiving end and the terminal end, wherein the first perforation set comprises:
      a first perforation portion extending in a first direction and terminating at an end point before reaching the first perimeter portion;
      a second perforation portion extending from the end point of the first perforation portion in a second direction different from the first direction.

2. The dressing of claim 1, wherein the body layer further comprises a support material.

3. The dressing of claim 2, wherein the support material covers a portion of the body layer.

4. The dressing of claim 2, wherein the support material extends to the first perimeter portion and the second perimeter portion.

5. The dressing of claim 2, the support material is less elastic than the body layer.

6. The dressing of claim 2, wherein the first perforation set is a plurality of cuts that each extend through the support material and at least partially extend through the body layer.

7. The dressing of claim 1, further comprising a second perforation set extending at least partially through the body layer.

8. The dressing of claim 7, wherein the second perforation set extends from the second perimeter portion.

9. The dressing of claim 7, wherein the first perforation set has a first end and a second end, and the second perforation set has a first end and a second end.

10. The dressing of claim 1, wherein the second perimeter portion defines:
    a first width of the slot at the receiving end thereof; and
    a second width of the slot between the terminal and receiving ends thereof, wherein the second width is greater than the first width.

11. The dressing of claim 10, wherein the second perimeter portion defines a bulbous portion of the slot having the second width, and wherein the first perforation set extends from the bulbous portion.

12. The dressing of claim 1, wherein the body layer comprises one or more layers.

13. The dressing of claim 1, wherein the slot separates first and second portions of the body layer that are symmetrical about the slot axis.

14. The dressing of claim 1, wherein the first perforation set is a plurality of cuts that each extend entirely through the thickness of the body layer.

15. The dressing of claim 1, wherein the body layer further comprises a window.

16. The dressing of claim 1, wherein the first perforation portion extends in the first direction perpendicular to the slot axis.

17. A system for securing a device comprising:
the medical dressing of claim 1; and
the device overlying a substrate;
wherein the dressing overlies the device and secures to the substrate and
wherein the device aligns with the slot.

18. A method of securing a device to a substrate comprising: applying the dressing of claim 1 to the device and the substrate;
wherein the device aligns with the slot.

* * * * *